(12) United States Patent
Hale

(10) Patent No.: US 12,370,343 B2
(45) Date of Patent: Jul. 29, 2025

(54) REFRESHING STYLETS, CATHETER SYSTEMS, AND METHODS THEREOF

(71) Applicant: Bard Peripheral Vascular, Inc., Franklin Lakes, NJ (US)

(72) Inventor: Niki Hale, Bountiful, UT (US)

(73) Assignee: Bard Peripheral Vascular, Inc., Franklin Lakes, NJ (US)

(*) Notice: Subject to any disclaimer, the term of this patent is extended or adjusted under 35 U.S.C. 154(b) by 0 days.

(21) Appl. No.: 18/621,887

(22) Filed: Mar. 29, 2024

(65) Prior Publication Data
US 2024/0238559 A1 Jul. 18, 2024

Related U.S. Application Data

(62) Division of application No. 17/237,990, filed on Apr. 22, 2021, now Pat. No. 11,944,760.

(60) Provisional application No. 63/045,676, filed on Jun. 29, 2020.

(51) Int. Cl.
*A61M 25/01* (2006.01)
*A61M 25/00* (2006.01)
*A61M 25/09* (2006.01)

(52) U.S. Cl.
CPC ...... *A61M 25/0102* (2013.01); *A61M 25/007* (2013.01); *A61M 2025/091* (2013.01); *A61M 2202/0275* (2013.01); *A61M 2205/05* (2013.01)

(58) Field of Classification Search
CPC ............ A61M 25/0102; A61M 25/007; A61M 2025/091; A61M 2202/0275; A61M 2205/05; A61M 2025/0056; A61M 2025/0063; A61M 2025/0079; A61M 25/0017; A61M 2025/0019
See application file for complete search history.

(56) References Cited

U.S. PATENT DOCUMENTS

| | | | |
|---|---|---|---|
| 4,639,246 | A | 1/1987 | Dudley |
| 2005/0124970 | A1 | 6/2005 | Kunin et al. |
| 2006/0058737 | A1 | 3/2006 | Herweck et al. |
| 2015/0051583 | A1 | 2/2015 | Horvath et al. |
| 2018/0161546 | A1 | 6/2018 | Aslam et al. |
| 2019/0184136 | A1 | 6/2019 | Lubinski et al. |
| 2021/0402145 | A1 | 12/2021 | Hale |

OTHER PUBLICATIONS

U.S. Appl. No. 17/237,990, filed Apr. 22, 2021 Final Office Action dated Oct. 17, 2023.

(Continued)

*Primary Examiner* — James D Ponton
(74) *Attorney, Agent, or Firm* — Rutan & Tucker LLP

(57) ABSTRACT

Refreshing stylets, catheter systems, and methods thereof. The refreshing stylet can be configured to fit within a lumen of a catheter such as hemodialysis catheter. The refreshing stylet can include an elongated hollow body having a proximal portion coupled to a needleless connector, a distal portion ending in a distal tip, an interior surface, an exterior surface, and a side hole. The exterior surface can be coated with a sustained-release formulation including one or more anti-thrombotic agents. The sustained-release formulation can be configured to contact a luminal surface of the catheter and prevent thrombus formation thereon. The side hole can be configured to provide a locking solution to the lumen of the catheter for locking the catheter between uses.

8 Claims, 6 Drawing Sheets

(56) References Cited

OTHER PUBLICATIONS

U.S. Appl. No. 17/237,990, filed Apr. 22, 2021 Non Final Office Action dated Jun. 20, 2023.
U.S. Appl. No. 17/237,990, filed Apr. 22, 2021 Notice of Allowance dated Jan. 4, 2024.

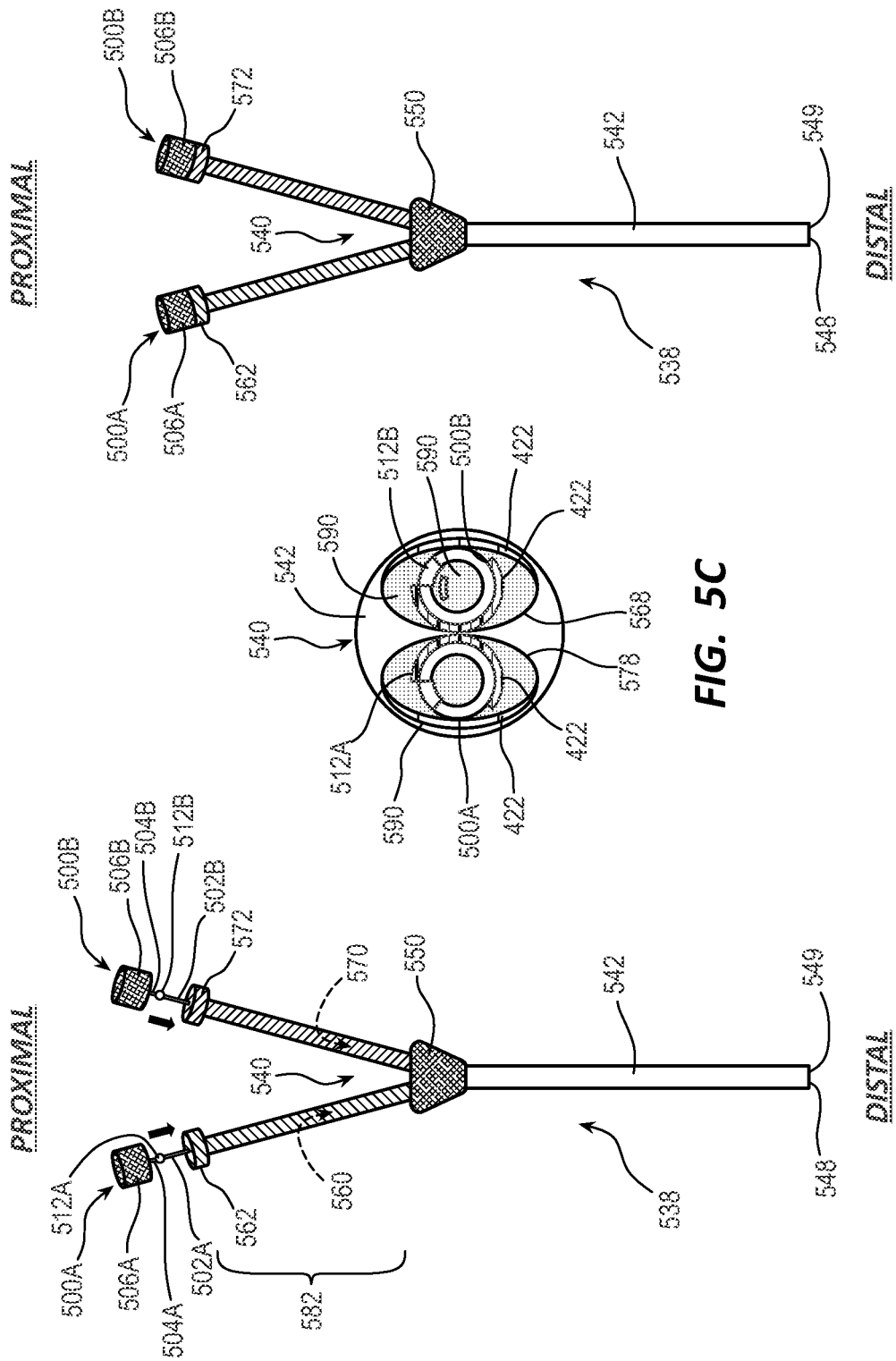

REFRESHING STYLETS, CATHETER SYSTEMS, AND METHODS THEREOF

PRIORITY

This application is a division of U.S. patent application Ser. No. 17/237,990, filed Apr. 22, 2021, now U.S. Pat. No. 11,944,760, which claims the benefit of priority to U.S. Provisional Application No. 63/045,676, filed Jun. 29, 2020, each of which is incorporated by reference in its entirety into this application.

BACKGROUND

Catheter-related thrombosis and fibrin-sheath formation are known causes of hemodialysis-catheter failure. The current treatment of these conditions, once identified, include prophylaxis with thrombolytic flushes or catheter replacement. To prevent thrombosis and fibrin-sheath formation, many health care providers treat catheter lumens with a locking solution in between dialysis sessions. These locking solutions can include sodium citrate or heparin. However, these solutions can lose their efficacy over time. It would beneficial to be able to deliver consistent antithrombotic agents to the catheter lumens in between dialysis sessions to prevent catheter-related thrombosis and fibrin-sheath formation.

Disclosed herein are refreshing stylets, catheter systems, and methods of use that address the foregoing.

SUMMARY

Disclosed herein is a refreshing stylet configured to fit within a lumen of a catheter. The refreshing stylet includes, in some embodiments, an elongated hollow body. The hollow body includes a proximal portion coupled to a needleless connector. The hollow body also includes a distal portion ending in a distal tip, an interior surface, an exterior surface, and a side hole. The exterior surface is coated with a sustained-release formulation including one or more anti-thrombotic agents. The sustained-release formulation is configured to contact a luminal surface of the catheter and prevent thrombus formation thereon. The side hole is through the hollow body and connects the interior surface with the exterior surface. The side hole is configured to provide a locking solution to the lumen of the catheter for locking the catheter between uses.

In some embodiments, the side hole is positioned so that an entirety of the lumen of the catheter can be filled with a set volume of the locking solution through the side hole.

In some embodiments, the side hole is located in the proximal portion.

In some embodiments, the side hole is part of a plurality of side holes.

In some embodiments, the plurality of side holes is located in the proximal portion.

In some embodiments, the plurality of side holes are organized in an array along a length of the stylet.

In some embodiments, the plurality of side holes are organized into pairs of side holes.

In some embodiments, the pairs of side holes are positioned longitudinally along the hollow body.

In some embodiments, the pairs of side holes are positioned circumferentially around the hollow body in one or more locations along a length of the hollow body.

In some embodiments, the pairs of side holes spiral around the hollow body.

In some embodiments, the distal tip is closed.

In some embodiments, the distal portion of the hollow body is coated with the sustained-release formulation. The one-or-more antithrombotic agents of the sustained-release formulation are selected from the group consisting of nitric oxide, tissue plasminogen activator ("TPA"), and heparin.

In some embodiments, the sustained-release formulation is covalently bonded to the hollow body.

In some embodiments, the sustained-release formulation includes the nitric oxide dissolved within the sustained-release formulation such that the nitric oxide controllably off gasses.

Also disclosed herein is a catheter system including, in some embodiments, a hemodialysis catheter and a refreshing stylet configured to fit within at least one lumen of the catheter. The hemodialysis catheter includes a hub coupled to a catheter tube having the-at-least-one lumen. The refreshing stylet includes an elongated hollow body. The hollow body includes a proximal portion coupled to a needleless connector. The hollow body also includes a distal portion ending in a distal tip, an interior surface, an exterior surface, and a side hole.

The exterior surface is coated with a sustained-release formulation including one or more anti-thrombotic agents. The sustained-release formulation is configured to contact a luminal surface of the catheter and prevent thrombus formation thereon. The side hole is through the hollow body and connects the interior surface with the exterior surface. The side hole is configured to provide a locking solution to the at-least-one lumen of the catheter for locking the catheter between uses.

In some embodiments, the side hole is part of a plurality of side holes located in the distal portion of the hollow body. The plurality of side holes are configured to convey a fluid from the refreshing stylet to the at-least-one lumen of the catheter.

In some embodiments, the side hole is part of a plurality of side holes located in the proximal portion of the hollow body. The plurality of side holes are configured to convey a fluid from the refreshing stylet to the at-least-one lumen of the catheter.

In some embodiments, the one-or-more anti-thrombotic agents of the sustained-release formulation are selected from the group consisting of nitric oxide, TPA, and heparin.

In some embodiments, the sustained-release formulation includes the nitric oxide dissolved within the sustained-release formulation. The sustained-release formulation is configured to controllably off gas the nitric oxide into the luminal surface of the catheter to prevent the thrombus formation thereon.

In some embodiments, the sustained-release formulation coats a terminal portion of the distal portion of the refreshing stylet such that the refreshing stylet refreshes a commensurate portion of the at-least-one lumen of the catheter when inserted therein.

In some embodiments, the sustained-release formulation is timely released over a range of 24-72 hours into the at-least-one lumen of the catheter.

Also disclosed herein is a method of using a refreshing stylet in a catheter system. The method includes a first stylet-obtaining step, a first stylet-inserting step, a first needless connector-attaching step, and a first lumen-filling step. The first stylet-obtaining step includes obtaining a first refreshing stylet. The first stylet-inserting step includes inserting the first refreshing stylet into an arterial lumen of a hemodialysis catheter such that the first refreshing stylet contacts an arterial-lumen surface with a sustained-release formulation. The sustained-release formulation has one-or-more anti-thrombotic agents coated on an exterior surface of the first refreshing stylet. The first needless connector-attaching step includes attaching a first needless connector coupled to a proximal portion of the first refreshing stylet to an arterial Luer connector of the hemodialysis catheter. The first needless connector-attaching step ensures an airtight seal of the arterial lumen. The first lumen-filling step includes filling the arterial lumen with a set volume of locking solution. The first lumen-filling step is effectuated by flowing the locking solution from a syringe into the first needless connector, through an elongated hollow body of the first refreshing stylet, and out a first side hole into the arterial lumen.

In some embodiments, the first lumen-filling step includes flowing the locking solution out of a plurality of side holes including the first side hole located in a proximal portion of the hollow body.

In some embodiments, the first lumen-filling step includes flowing the locking solution out of a plurality of side holes including the first side hole located in a distal portion of the hollow body.

In some embodiments, the sustained-release formulation covers a terminal portion of a distal portion of the first refreshing stylet such that the first refreshing stylet refreshes a commensurate portion of the arterial-lumen surface of the hemodialysis catheter when inserted therein.

In some embodiments, the one-or-more anti-thrombotic agents are selected from the group consisting of nitric oxide, TPA, and heparin.

In some embodiments, the sustained-release formulation includes the nitric oxide dissolved within the sustained-release formulation. The sustained-release formulation is configured to controllably off gas the nitric oxide into the arterial-lumen surface to prevent the thrombus formation thereon.

In some embodiments, the method further includes a first stylet-replacing step. The first stylet-replacing step includes replacing the first refreshing stylet in the arterial lumen within a predetermined amount of time or after hemodialysis.

In some embodiments, the method includes a second stylet-obtaining step, a second stylet-inserting step, a second needless connector-attaching step, a second lumen-filling step, and second stylet-replacing step. The second stylet-obtaining step includes obtaining a second refreshing stylet. The second stylet-inserting step includes inserting the second refreshing stylet into a venous lumen of the hemodialysis catheter such that the second refreshing stylet contacts a venous-lumen surface with the sustained-release formulation also coated on an exterior surface of the second refreshing stylet. The second needless connector-attaching step includes attaching a second needless connector coupled to a proximal portion of the second refreshing stylet to a venous Luer connector of the hemodialysis catheter. The second needless-connector step ensures an airtight seal of the venous lumen. The second lumen-filling step includes filling the venous lumen with another set volume of the locking solution. The second lumen-filling step is effectuated by flowing the locking solution from a same or different syringe into the second needless connector, through an elongated hollow body of the second refreshing stylet, and out a second side hole into the venous lumen. The second stylet-replacing step includes replacing the first refreshing stylet in the arterial lumen within a predetermined amount of time or after hemodialysis.

These and other features of the concepts provided herein will become more apparent to those of skill in the art in view of the accompanying drawings and following description, which describe particular embodiments of such concepts in greater detail.

BRIEF DESCRIPTION OF DRAWINGS

FIG. 5A illustrates a catheter system including a pair of refreshing stylets partially disposed in a catheter in accordance with some embodiments.

FIG. 5B illustrates a catheter system including a pair of refreshing stylets fully disposed in the catheter and locked thereto in accordance with some embodiments.

FIG. 5C illustrates a transverse cross section of the catheter system of FIG. 5A or 5B in accordance with some embodiments.

DESCRIPTION

Figures 1A, 1B:
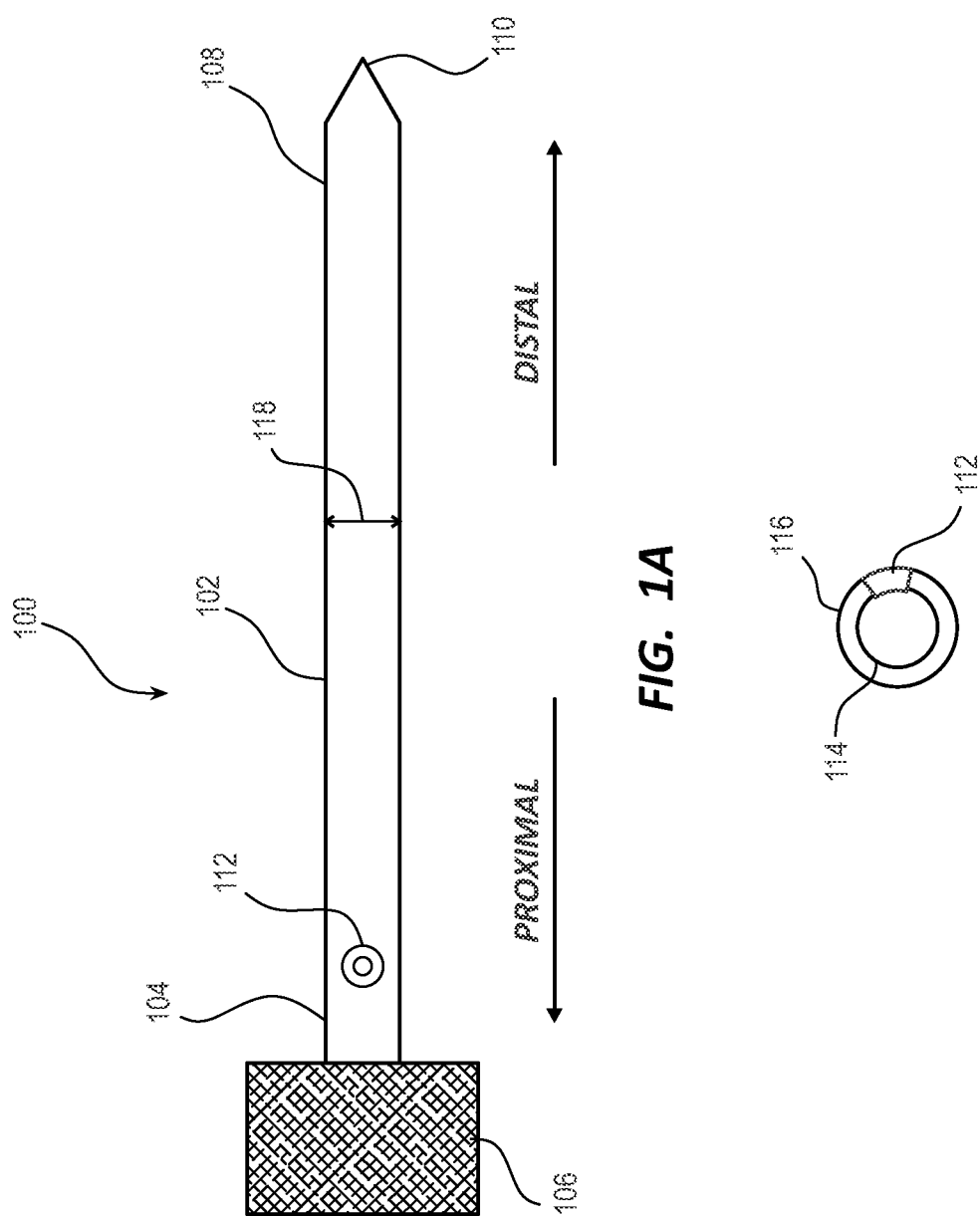
FIG. 1A illustrates a refreshing stylet in accordance with some embodiments.
FIG. 1B illustrates a transverse cross section of the refreshing stylet of FIG. 1A in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Refreshing Stylets

A refreshing stylet is configured for contacting a luminal surface of a catheter with a sustained-release formulation when disposed in a lumen of a catheter. The sustained-release formulation includes one-or-more anti-thrombotic agents useful for treating the surface of the lumen between procedures with the catheter to prevent catheter-related thrombosis and fibrin sheath formation in the lumen. Advantageously, the refreshing stylet can also be configured for filling the lumen with a set volume of locking solution while the stylet is disposed within the lumen the lumen of the catheter. This is particularly advantageous for hemodialysis catheters.

FIG. 1A illustrates a refreshing stylet 100 in accordance with some embodiments.

As shown, the refreshing stylet 100 includes an elongated hollow body or tube 102 having a proximal portion 104 and a distal portion 108. Being hollow, the hollow body 102 includes both an interior surface 114 and an exterior surface 116 with a sustained-release formulation 422 including the one-or-more anti-thrombotic agents thereon. (See FIGS. 1B, 4B, and 4C.) The refreshing stylet 100 also includes at least one side hole 112 through a side of the hollow body 102 that connects the interior surface 114 with the exterior surface 116. The proximal portion 104 of the refreshing stylet 100 is coupled to a needless connector 106. The needless connector 106 can include a Luer connector configured to connect a syringe without a needle and allow passage of fluid from the syringe. The distal portion 108 ends with a distal tip 110 that can have an open or closed end. The side hole 112 is configured to convey the fluid from the hollow body 102 to the lumen of the catheter. For example, the fluid can be a locking solution for locking a hemodialysis catheter between uses. When the distal tip 110 has a closed end, the distal tip 110 advantageously directs the fluid from the syringe through the side hole 112 into the lumen of the catheter, thereby promoting distribution of the fluid in the lumen of the catheter.

FIG. 1B illustrates a transverse cross section of the hollow body 102 of refreshing stylet of FIG. 1A in accordance with some embodiments.

As set forth above, the hollow body 102 includes the interior surface 114 and the exterior surface 116. The side hole 112 connects the interior surface 114 of the hollow body 102 with the exterior surface 116 thereof and allows fluid communication between the interior surface 114 and the exterior surface 116 when the refreshing stylet 100 is disposed within a lumen of a catheter.

The interior surface 114 or the exterior surface 116 can be textured over a portion of the hollow body 102. For example, the interior surface 114 can include indentations or channels over a portion of the proximal portion 104, the distal portion 108, or a combination thereof to promote turbulent of laminar flow to facilitate fluid flow from the interior surface 114 to the exterior surface 116 through the side hole 112. For example, the exterior surface 116 can include indentations or channels over a portion of the proximal portion 104, the distal portion 108, or a combination thereof to likewise facilitate fluid flow over the exterior surface 116 of the refreshing stylet 100. Alternatively or additionally, when the exterior surface 116 is textured, the exterior surface 116 can facilitate adherence of the sustained-release formulation thereon. That said, each surface or the interior surface 114 and the exterior surface 116 can be smooth without any added texture.

FIGS. 2A-2D illustrate the refreshing stylet 100 with the side hole 112 or a plurality of side holes 212 in various locations along the hollow body 102 in accordance with some embodiments.

Figure 2A:
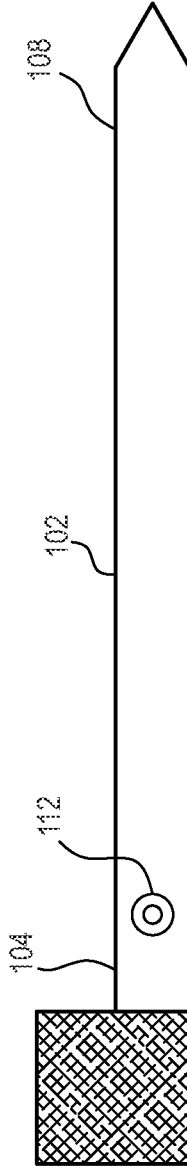
FIG. 2A illustrates a refreshing stylet with a side hole in a proximal portion of the refreshing stylet in accordance with some embodiments.
Figure 2B:
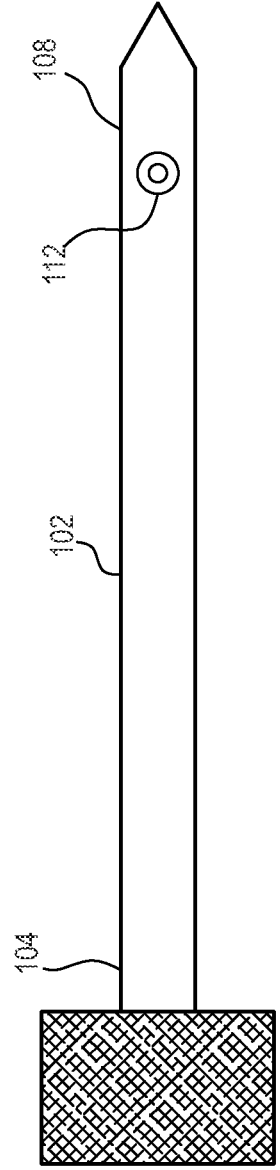
FIG. 2B illustrates a refreshing stylet with a side hole in a distal portion of the refreshing stylet in accordance with some embodiments.

As shown in FIG. 2A, the refreshing stylet 100 can include the side hole 112 located in the proximal portion 104 of the hollow body 102. Alternatively, the refreshing stylet 100 can include the side hole 112 located in the distal portion 108 of the hollow body 102 near the distal tip 110 as shown in FIG. 2B. However, the locations are not limited thereto. Indeed, the side hole 112 can be located in both the proximal portion 104 and the distal portion 108 of the hollow body 102, as well as therebetween. The side hole 112 is ideally positioned in the hollow body 102 such that an entirety of a lumen of a catheter (e.g., hemodialysis) can be filled with a set volume of a fluid (e.g., a locking solution) through the side hole 112.

Figure 2C:
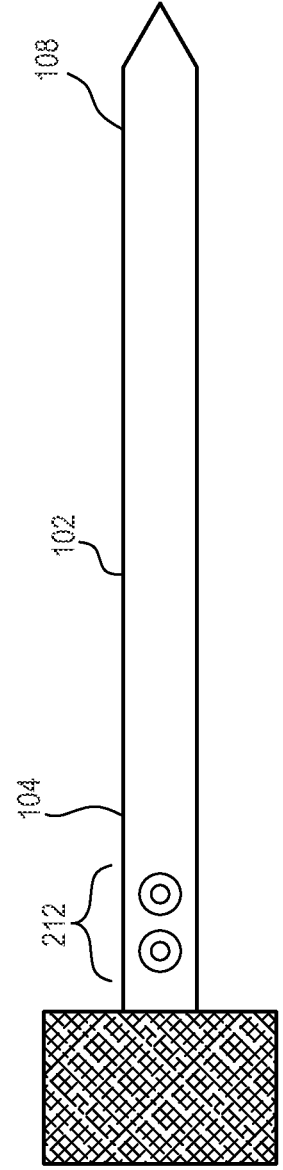
FIG. 2C illustrates a refreshing stylet with a plurality of side holes in a proximal portion of the refreshing stylet in accordance with some embodiments.
Figure 2D:
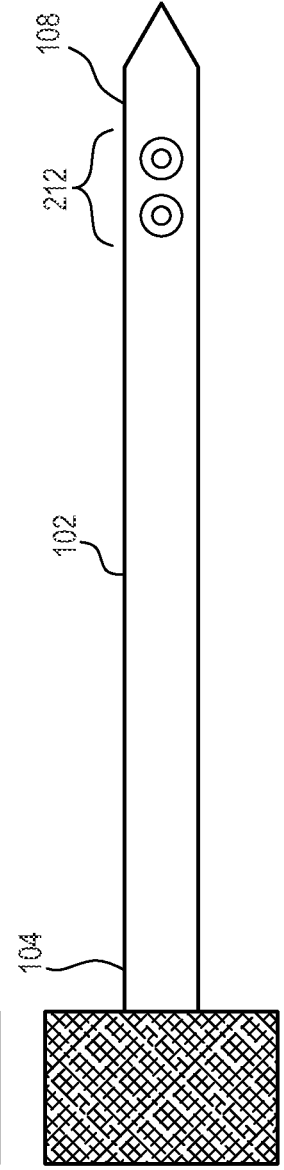
FIG. 2D illustrates a refreshing stylet with a plurality of side holes in a distal portion of the refreshing stylet in accordance with some embodiments.

The side hole 112 can be part of the plurality of side holes 212. As shown in FIG. 2C, the refreshing stylet 100 can include the plurality of side holes 212 located in the proximal portion 104 of the hollow body 102. Alternatively, the refreshing stylet 100 can include the plurality of side holes 212 located in the distal portion 108 of the hollow body 102 near the distal tip 110 as shown in FIG. 2D. However, the locations are not limited thereto.

Indeed, the plurality of side holes 212 can be located in both the proximal portion 104 and the distal portion 108 of the hollow body 102, as well as therebetween. The plurality of side holes 212 is ideally positioned in the hollow body 102 such that an entirety of a lumen of a catheter (e.g., hemodialysis) can be filled with a set volume of a fluid (e.g., a locking solution) through the plurality of side holes 212.

In addition to the various locations of the plurality of side holes 212, the plurality of side holes 212 can have various arrangements. For example, the plurality of side holes 212 can be longitudinally arranged or organized such as in an array along a length of the hollow body 102. The plurality of side holes 212 can be alternatively arranged or organized into one or more pairs of side holes. If more than one pair of side holes, the pairs of side holes can be longitudinally arranged or organized into the pairs of side holes along the length of the hollow body 102. The pairs of side holes can be alternatively circumferentially arranged or organized into the pairs of side holes around the hollow body 102, optionally along the length of the hollow body 102. The pair of side holes can even spiral around the hollow body 102 in such an arrangement. (See FIGS. 4A-4C.)

Each side hole of the side hole 112 and the plurality of side holes 212 can have a shape and size configured to facilitate flow of the fluid through the side hole 112 or the plurality of through holes 212 and into the lumen of the catheter. For example, each side hole of the side hole 112 and the plurality of side holes 212 can independently be a circle, oval, triangle, square, pentagon, or some other shape. As to size, each side hole of the side hole 112 and the plurality of side holes 212 can Independently be in a range of 0.001-10 mm.

Figures 3A, 3B, 3C, 3D:
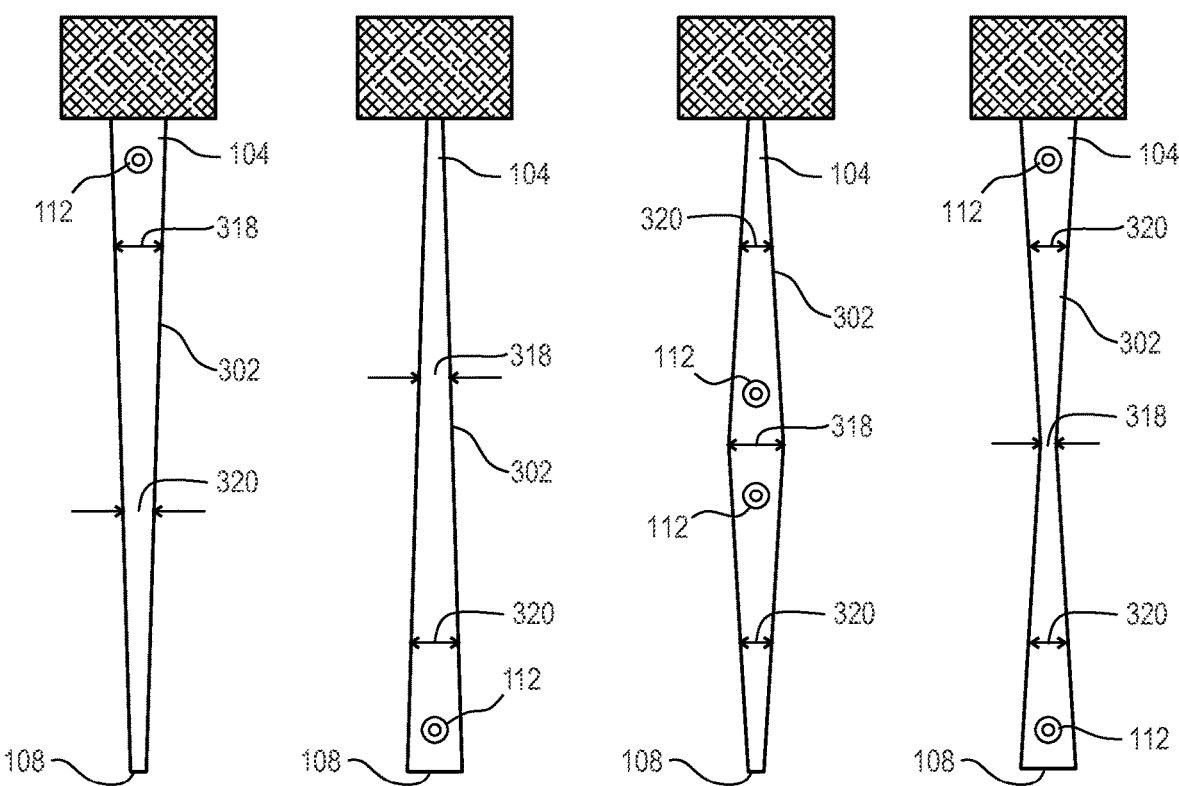
FIG. 3A illustrates a refreshing stylet having an elongate hollow tube with a first profile in accordance with some embodiments.
FIG. 3B illustrates a refreshing stylet having an elongate hollow tube with a second profile in accordance with some embodiments.
FIG. 3C illustrates a refreshing stylet having an elongate hollow tube with a third profile in accordance with some embodiments.
FIG. 3D illustrates a refreshing stylet having an elongate hollow tube with a fourth profile in accordance with some embodiments.

FIGS. 3A-3C illustrate a hollow tube 302 of the refreshing stylet 100 having various profiles in accordance with some embodiments. It should be understood features of the hollow tube 102 set forth above are shared by the hollow tube 302; however, the hollow tube 302 is differentiated from the hollow tube 102 in that the hollow tube 302 has a different profile.

As shown, the hollow body 302 of the refreshing stylet 100 can include a first diameter 318 and a second diameter 320. The hollow body 102 of the refreshing stylet 100 shown in FIGS. 1A and 2A-2D also includes a first diameter 118; however, any second diameter such as the second diameter 320 is commensurate with the first diameter 118 as the refreshing stylet 100 of FIGS. 1A and 2A-2D has a consistent profile from the proximal portion 104 of the refreshing stylet 100 to the distal portion 108 of the refreshing stylet 100 within the range of 1-26 Fr depending upon a type and size of catheter. Such a consistent profile is configured to allow the hollow body 102 to contact a luminal surface of a catheter simultaneously at multiple locations with the sustained-release formulation if applied over an entirety of the hollow body 102 or in multiple locations thereof. Alternatively, the first diameter 318 and the second diameter 320 can be different, thereby providing different profiles of the refreshing stylet 100 from the proximal portion 104 to the distal portion 108 thereof. The different profiles are configured to allow the hollow body 302 to contact a luminal surface of a catheter at selective locations with the sustained-release formulation over other locations of the luminal surface.

FIG. 3A illustrates the hollow body 302 of the refreshing stylet 100 with a taper from the proximal portion 104 of the hollow body 302 to the distal portion 108 of the hollow body 302. As such, the first diameter 318 is greater than the second diameter 320. FIG. 3B illustrates the hollow body 302 of the refreshing stylet with a reverse taper from the proximal portion 104 of the hollow body 302 to the distal portion 108 thereof. As such, the first diameter 318 is less than the second diameter 320. Variations of the foregoing are also possible. FIG. 3C illustrates the hollow body 302 of the refreshing stylet 100 with a reverse taper from the proximal portion 104 up to a medial potion of the hollow body 302 and a taper from the medial portion up to the distal portion 108 of the hollow body 302. As shown, the first diameter 318 indicated in the medial portion of the hollow body 302 is greater than the second diameter 320 in either the proximal portion 104 of the hollow body 302 or the distal portion 108 thereof.

FIG. 3D illustrates the hollow body 302 of the refreshing stylet 100 with a taper from the proximal portion 104 up to a medial potion of the hollow body 302 and a reverse taper from the medial portion up to the distal portion 108 of the hollow body 302. As shown, the first diameter 318 indicated in the medial portion of the hollow body 302 is less than the second diameter 320 in either the proximal portion 104 of the hollow body 302 or the distal portion 108 thereof. Again, the different profiles are configured to allow the hollow body 302 to contact a luminal surface of a catheter at selective locations with the sustained-release formulation over other locations of the luminal surface.

Figure 4A:
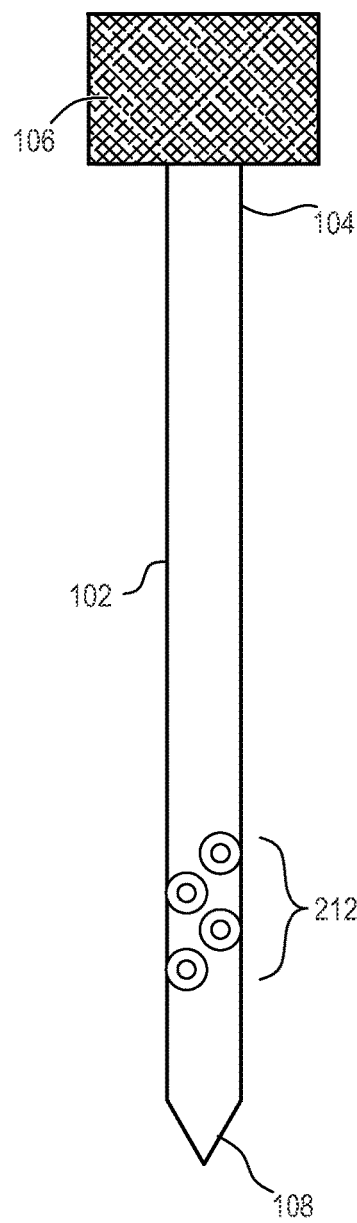
FIG. 4A illustrates a refreshing stylet without a sustained-release formulation coating a distal portion of the refreshing stylet in accordance with some embodiments.
Figure 4B:
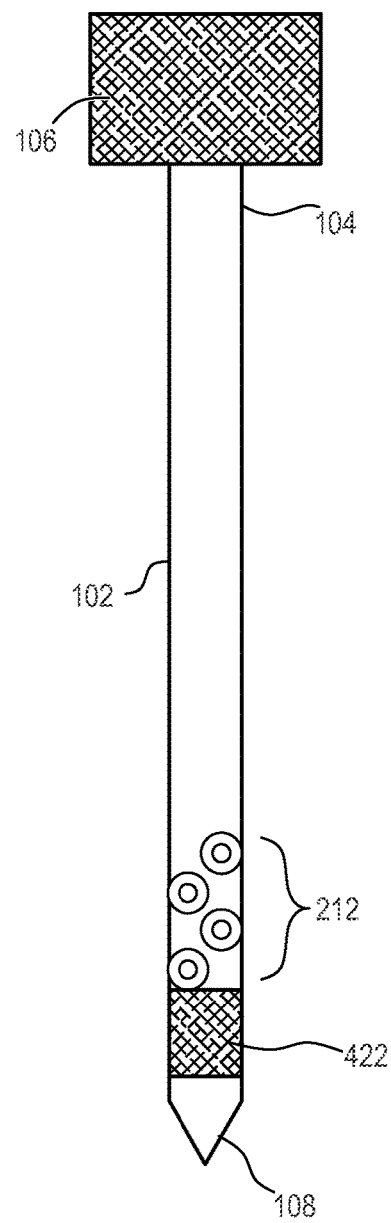
FIG. 4B illustrates the refreshing stylet of FIG. 4A with a sustained-release formulation coating a distal portion of the refreshing stylet in accordance with some embodiments.
Figure 4C:
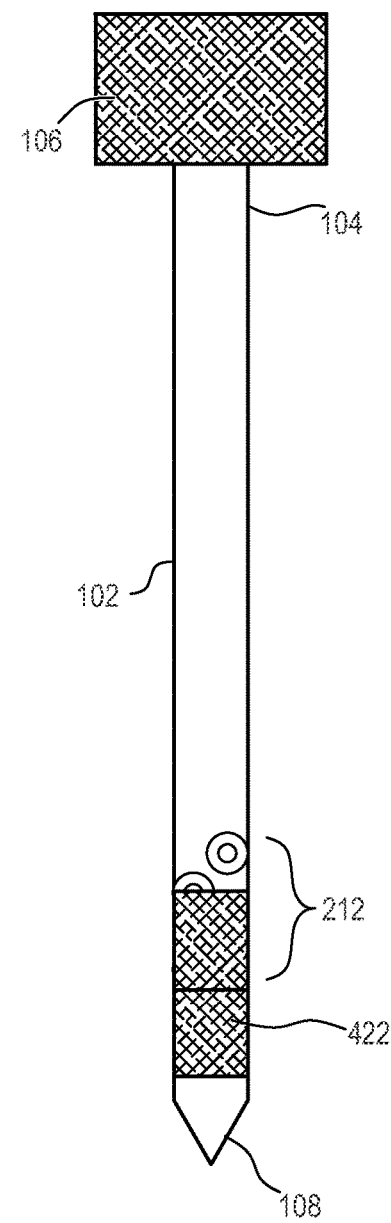
FIG. 4C illustrates the refreshing stylet of FIG. 4A with the sustained-release formulation coating more of the distal portion of the refreshing stylet in accordance with some embodiments.

FIGS. 4A-4C illustrate the refreshing stylet 100 with different applications of the sustained-release formulation 422 on the refreshing stylet 100 in accordance with some embodiments. Alternatively, FIGS. 4A-4C illustrate the refreshing stylet 100 with the sustained-release formulation 422 on the refreshing stylet 100 after different amounts of time in use in accordance with some embodiments.

The sustained-release formulation 422 can coat any portion of the hollow body 102 ranging from the proximal portion 104 to the distal portion 108 up to an entirety of the hollow body 102. However, since thrombosis and fibrinsheath formation typically occurs in the distal portion of catheters such as hemodialysis catheters, selective application of the sustained-release formulation 422 on the distal portion 108 of the refreshing stylet 100 (e.g., a terminal portion of the refreshing stylet 100) reasonably balances efficacy and cost effectiveness.

Beginning with FIG. 4C, FIG. 4C. illustrates the refreshing stylet 100 with the sustained-release formulation 422 coating the distal portion 108 of the hollow body 102 including around the side hole 112 or the plurality of side holes 212. Alternatively, FIG. 4C illustrates the refreshing stylet 100 with the sustained-release formulation 422 coating the distal portion 108 of the hollow body 102 before the refreshing stylet 100 is disposed in a lumen of a catheter or soon thereafter, where little to none of the sustained-release formulation 422 has been released from the exterior surface 116 of the hollow body 102.

Continuing with FIG. 4B, FIG. 4B. illustrates the refreshing stylet 100 with the sustained-release formulation 422 coating the distal portion 108 of the hollow body 102 distal of the side hole 112 or the plurality of side holes 212. Alternatively, FIG. 4B illustrates the refreshing stylet 100 with the sustained-release formulation 422 coating the distal portion 108 of the hollow body 102 at some time after the refreshing stylet 100 has been disposed in the lumen of the catheter, where some of the sustained-release formulation 422 has been released from the exterior surface 116 of the hollow body 102. It should be understood FIG. 4B is a pictorial representation. The sustained-release formulation 422 need not sustainably release in a proximal to distal direction. Indeed, the sustained-release formulation 422 formulation slowly releases over an entirety of the portion of the hollow body 102 it coats.

Lastly, FIG. 4A illustrates the refreshing stylet 100 without the sustained-release formulation 422 coating the distal portion 108 of the hollow body 102. Alternatively, FIG. 4A illustrates the refreshing stylet 100 at some time after (e.g., about 24-72 hours after) the refreshing stylet 100 has been disposed in the lumen of the catheter, where most of the sustained-release formulation 422 has been released from the exterior surface 116 of the hollow body 102.

The sustained-release formulation 422 can include one or more anti-thrombotic agents selected from the group consisting of nitric oxide, TPA, and heparin, and the sustained-release formulation can be formulated to non-covalently or covalently coat the exterior surface 116 of the hollow body 102. In one example, the sustained-release formulation 422 includes nitric oxide. The nitric oxide can be dissolved within the sustained-release formulation 422 such that the nitric oxide controllably off gasses over time into a luminal surface of a catheter when the refreshing stylet 102 is disposed in the catheter. However, the sustained-release formulation 422 is not limited to the foregoing one-or-more anti-thrombotic agents. Indeed, any anti-thrombotic agent can be used in the sustained-release formulation 422.

Catheter Systems

FIGS. 5A and 5B illustrate a catheter system 540 including a pair of refreshing stylets 500A and 500B disposed in a catheter 538 in accordance with some embodiments. FIG. 5C illustrates a transverse cross section of the catheter system 540 of FIG. 5A or 5B in accordance with some embodiments.

As shown, the catheter system 540 includes the catheter 538 (e.g., hemodialysis catheter) and the pair of refreshing stylets 500A and 500B, each of which stylets—like the refreshing stylet 100—is configured to fit within a lumen of the catheter 538 to contact a luminal surface thereof with the sustained-release formulation 422 and prevent thrombus or fibrin-sheath formation therein.

The catheter 538 includes a hub 550 coupled to a catheter tube 542 having a first lumen 560, a second lumen 570, and a plurality of extension legs 582 coupled to Luer connectors (e.g., Luer connectors 562 and 572). In the case of a hemodialysis catheter, which is used herein as an example, the first lumen 560 is an arterial lumen and the second lumen 570 is a venous lumen. As such, the first lumen 560 and the second lumen 570 are also referred to as the arterial lumen 560 and the venous lumen 570.

As set forth above with respect to the refreshing stylet 100, the refreshing stylet 500A and the refreshing stylet 500B respectively include a hollow body 502A and 502B including a proximal portion 504A and 504B coupled to a needleless connector 506A and 506B, and a side hole 512A and 512B. In addition, each refreshing stylet of the refreshing stylet 500A and the refreshing stylet 500B include the sustained-release formulation 422. The refreshing stylet 500A is disposed within the arterial lumen 560 and the refreshing stylet 500B is disposed within the venous lumen 570 when the catheter system 540 is in use (e.g., locked with the locking solution 590 after a hemodialysis procedure) as set forth in more detail below. It should be understood the description set forth above for the refreshing stylet 100 extends to the refreshing stylets 500A and 500B.

The refreshing stylet 500A is configured to be inserted into the arterial lumen 560 such that when fully inserted the distal tip of the hollow body 502A extends to but not through a distal opening 548 of the arterial lumen 560. The refreshing stylet 500B is likewise configured to be inserted into the venous lumen 570 such that when fully inserted the distal tip of the hollow body 502B extends to but not through a distal opening 549 of the venous lumen 570. However, in other embodiments, the refreshing stylet 500A or 500B is configured to be inserted into the arterial lumen 560 or the venous lumen 570 such that when fully inserted the distal tip extends through the distal opening 548 or 549. Still, in other embodiments, the refreshing stylet 500A or 500B is configured to be inserted into the arterial lumen 560 or the venous lumen 570 such that when fully inserted the distal tip is short of the distal opening 548 or 549. The refreshing stylet 500A can be secured in the arterial lumen 560 by coupling the needleless connector 506A to the Luer connector 562, which effectuates full insertion of the refreshing stylet 500A in the arterial lumen 560. Likewise, the refreshing stylet 500B can be secured in the venous lumen 570 by coupling the needleless connector 506B to the Luer connector 572, which effectuates full insertion of the refreshing stylet 500B in the venous lumen 570.

As shown in FIG. 5C, the refreshing stylet 500A includes the sustained-release formulation 422 and the refreshing stylet 500B includes the sustained-release formulation 422. When the refreshing stylet 500A is disposed within the arterial lumen 560, the refreshing stylet 500A can treat a luminal surface 578 of the arterial lumen 560 with the sustained-release formulation 422 while providing a locking solution 590 (e.g., saline, a mixture of heparin and saline, a mixture of saline and sodium citrate, etc.) to the arterial lumen 560 from the hollow body 502A through the side hole 512A. Likewise, when the refreshing stylet 500B is disposed within the venous lumen 570, the refreshing stylet 500B can treat a luminal surface 568 of the venous lumen 570 with the sustained-release formulation 422 while providing the locking solution 590 to the venous lumen 570 from the hollow body 502B through the side hole 512B. After locking the catheter 538 with the locking solution 590, the refreshing stylets 500A and 500B can remain in the catheter 538 and continue to treat the luminal surfaces 578 and 568 with the sustained-release formulation 422.

When the refreshing stylet 500A is disposed within the arterial lumen 560 and the refreshing stylet 500B is disposed within the venous lumen 570, a portion of the refreshing stylet 500A can contact the luminal surface 578 of the arterial lumen 560 and a portion of the refreshing stylet 500B can contact the luminal surface 568 of the venous lumen 570. The portion of the refreshing stylet 500A that contacts the arterial-lumen surface 578 can be the distal portion, the proximal portion, or both. Preferably, the portion of the hollow body 502A configured to contact the arterial-lumen surface 578 is the same portion of the hollow body 502A that includes the sustained-release formulation 422. As such, the hollow body 502A can contact the arterial-lumen surface 578 with the sustained-release formulation 422 to refresh the arterial-lumen surface 578. Likewise, the portion of the refreshing stylet 500B that contacts the venous-lumen surface 568 can be the distal portion, the proximal portion, or both. Preferably, the portion of the hollow body 502B configured to contact the venous-lumen surface 568 is the same portion of the hollow body 502B that includes the sustained-release formulation 422. As such, the hollow body 502B can contact the venous-lumen surface 568 with the sustained-release formulation 422 to refresh the venous-lumen surface 568. The refreshing stylet 500A and the refreshing stylet 500B are configured to respectively contact the arterial lumen 560 and venous lumen 570 with the sustained-release formulation 422 only in distal portions of the lumens 560 and 570 when fully inserted into the lumens 560 and 570 and coupled to the Luer connectors 562 and 572 as shown in FIG. 5B.

Methods

Figure 6:
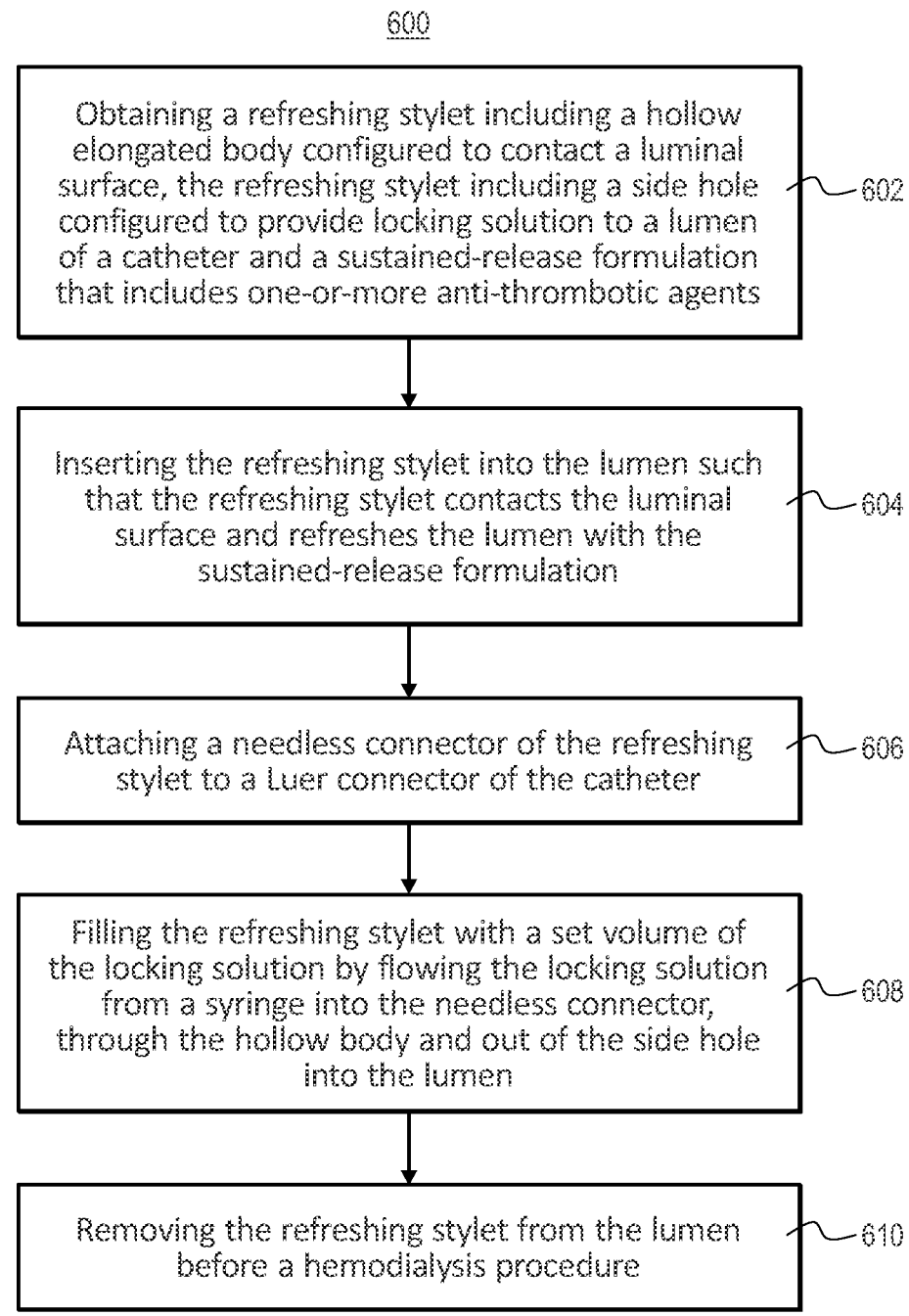
FIG. 6 illustrates a method of using a refreshing stylet in a catheter system in accordance with some embodiments.

FIG. 6 illustrates a first method 600 of using the refreshing stylet 500A or 500B in the catheter system 540 in accordance with some embodiments.

As shown, the method 600 includes an obtaining step 602. The obtaining step 602 includes obtaining the refreshing stylet 500A or 500B. As set forth above, the refreshing stylet 500A or 500B includes the hollow body 502A or 502B configured to contact the luminal surface (e.g., the arterial-lumen surface 578 or the venous-lumen surface 568) of the catheter 538, the hollow body 502A or 502B having the proximal portion thereof coupled to the needless connector 506A or 506B, the side hole 512A or 512B located in the proximal portion or distal portion configured to provide the locking solution 590 to the arterial lumen 560 or venous lumen 570, and the sustained-release formulation 422 including the one-or-more anti-thrombotic agents. The obtaining step 602 can include obtaining either one or both stylets of the refreshing stylets 500A and 500B as needed for refreshing one or both lumens of the arterial lumen 560 or the venous lumen 570 of the catheter 538. For example, if the catheter 538 includes the arterial lumen 560 and the venous lumen 570, the obtaining step 602 can include obtaining both the refreshing stylet 500A for the arterial lumen 560 and the refreshing stylet 500B for the venous lumen 570.

The method 600 also includes an inserting step 604. The inserting step 604 includes inserting the refreshing stylet 500A or 500B into the arterial lumen 560 or the venous lumen 570 of the catheter 538 such that the refreshing stylet 500A or 500B contacts the luminal surface 578 or 568 with the sustained-release formulation 422. The inserting step 604 can include inserting either one or both stylets of the refreshing stylets 500A and 500B into their respective lumens 560 and 570 as needed for refreshing one or both lumens of the arterial lumen 560 or the venous lumen 570 of the catheter 538. For example, if the catheter 538 includes the arterial lumen 560 and the venous lumen 570, the inserting step 604 can include inserting the refreshing stylet 500A into the arterial lumen 560 and the refreshing stylet 500B into the venous lumen 570 such as one after the other.

The method 600 also includes an attaching step 606. The attaching step 606 includes attaching the needless connector 506A or 506B of the refreshing stylet 500A or 500B to the Luer connector 562 or 572 of the catheter 538. The attaching step 606 can include twisting, joining, sliding, locking, or similar movements during the attaching step 606. Such twisting, sliding, or other movements are useful for positioning the refreshing stylet 500A or 500B within the lumen 560 or 570 for optimal contact of the luminal surface 568 or 570 with the sustained-release formulation 422. The attaching step 606 is important for creating a proper seal for locking the catheter 538.

The method 600 also includes a filling step 608. The filling step 608 includes filling the lumen 560 or 570 with a set volume of the locking solution 590 by flowing the locking solution 590 from a syringe into the needless connector 506A or 506B, through the hollow body 502A or 502B, out of the side hole 112A or 112B, or a plurality thereof, and into the lumen 560 or 570 while the refreshing stylet 500A and the refreshing stylet 500B are disposed therein. The filling step 608 can include coupling the syringe to the needless connector 506A or 506B before flowing the locking solution 590 into the needless connector 506A or 506B. The locking solution 590 can be alternatively or simultaneously injected into the arterial lumen 560 and the venous lumen 570 respectively by way of the needleless connectors 506A and 506B.

The method 600 also includes a removing step 610. The removing step 610 includes removing the refreshing stylet 500A or 500B from the lumen 560 or 570 before a hemodialysis procedure. The removing step 610 can include alternately or simultaneous removing the refreshing stylet 500A and 500B from the lumens 560 and 570 of the catheter 538. For example, the removing step 610 can include first removing the refreshing stylet 500A from arterial lumen 560 and then removing the refreshing stylet 500B from the venous lumen 570.

Notwithstanding the foregoing, a second method of using the refreshing stylet 500A or 500B in the catheter system 540 includes a first stylet-obtaining step, a first stylet-inserting step, a first needless connector-attaching step, and a first lumen-filling step. It should be understood the first method 600 and the second method set forth below are not mutually exclusive; that is, steps of the first method 600 or features thereof can be incorporated into the second method and vice versa.

The first stylet-obtaining step includes obtaining a first refreshing stylet such as the refreshing stylet 500A.

The first stylet-inserting step includes inserting the refreshing stylet 500A into the arterial lumen 560 of the catheter 538 (e.g., a hemodialysis catheter) such that the refreshing stylet 500A contacts the arterial-lumen surface 578 with the sustained-release formulation 422. The sustained-release formulation can cover a terminal portion of the distal portion of the refreshing stylet 500A such that the refreshing stylet 500A refreshes a commensurate portion of the arterial-lumen surface 578 of the catheter 538 when inserted therein. As set forth above, the sustained-release formulation 422 has one-or-more anti-thrombotic agents coated on the exterior surface of the refreshing stylet 500A.

The first needless connector-attaching step includes attaching a first needless connector such as the needless connector 506A coupled to the proximal portion of the refreshing stylet 500A to the arterial Luer connector 562 of the catheter 538. The first needless connector-attaching step ensures an airtight seal of the arterial lumen 560, which maintains a priming of the arterial lumen 560.

The first lumen-filling step includes filling the arterial lumen 560 with a set volume of the locking solution 590. The first lumen-filling step is effectuated by flowing the locking solution 590 from a syringe into the needless connector 506A, through the hollow body 502A of the refreshing stylet 500A, and out at least a first side hole (e.g., the side hole 512A) into the arterial lumen 560. Indeed, with respect to at least the first side hole, the first side hole can be part of a plurality of side holes (e.g., the plurality of side holes 212) such that the first lumen-filling step includes flowing the locking solution 590 out of the plurality of side holes including the first side hole. Such a plurality of side holes can be located in the proximal portion or the distal portion of the hollow body 502A.

The method can further include a first stylet-replacing step. The first stylet-replacing step includes replacing the refreshing stylet 500A in the arterial lumen 560 within a predetermined amount of time (e.g., 24-72 hours) or after a hemodialysis procedure.

The method can further include a second stylet-obtaining step, a second stylet-inserting step, a second needless connector-attaching step, a second lumen-filling step, and second stylet-replacing step.

The second stylet-obtaining step includes obtaining a second refreshing stylet such as the refreshing stylet 500B.

The second stylet-inserting step includes inserting the refreshing stylet 500B into the venous lumen 570 of the catheter 538 such that the refreshing stylet 500B contacts the venous-lumen surface 568 with the sustained-release formulation 422. The sustained-release formulation can cover a terminal portion of the distal portion of the refreshing stylet 500B such that the refreshing stylet 500B refreshes a commensurate portion of the venous-lumen surface 568 of the catheter 538 when inserted therein. As set forth above, the sustained-release formulation 422 has one-or-more anti-thrombotic agents coated on the exterior surface of the refreshing stylet 500B.

The second needless connector-attaching step includes attaching a second needless connector such as the needless connector 506B coupled to the proximal portion of the refreshing stylet 500B to the venous Luer connector 572 of the catheter 538. The second needless connector-attaching step ensures an airtight seal of the venous lumen 570, which maintains a priming of the venous lumen 570.

The second lumen-filling step includes filling the venous lumen 570 with a set volume of the locking solution 590. The first lumen-filling step is effectuated by flowing the locking solution 590 from a same or different syringe as that of the first lumen-filling step into the needless connector 506B, through the hollow body 502B of the refreshing stylet 500B, and out at least a second side hole (e.g., the side hole 512B) into the venous lumen 570. Indeed, with respect to at least the second side hole, the second side hole can be part of a plurality of side holes (e.g., the plurality of side holes 212) such that the second lumen-filling step includes flowing the locking solution 590 out of the plurality of side holes including the second side hole. Such a plurality of side holes can be located in the proximal portion or the distal portion of the hollow body 502B.

The second stylet-replacing step includes replacing the refreshing stylet 500B in the venous lumen 570 within the predetermined amount of time (e.g., 24-72 hours) or after the hemodialysis procedure.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures can be made from the particular embodiments disclosed herein without departing from the scope of the concepts provided herein.

What is claimed is:

1. A method of using a refreshing stylet in a catheter system, comprising:

obtaining a first refreshing stylet;

inserting the first refreshing stylet into an arterial lumen of a hemodialysis catheter such that the first refreshing stylet contacts a surface of the arterial lumen of the hemodialysis catheter with a sustained-release formulation having one or more anti-thrombotic agents coated on an exterior surface of the first refreshing stylet;

attaching a first needless connector coupled to a proximal portion of the first refreshing stylet to an arterial Luer connector of the hemodialysis catheter to ensure an airtight seal of the arterial lumen; and filling the arterial lumen with a first set volume of locking solution by flowing the locking solution from a syringe into the first needless connector, through an elongated hollow body of the first refreshing stylet, and out a first side hole into the arterial lumen.

2. The method according to claim 1, wherein the first side hole is located in a proximal portion of the elongated hollow body, and wherein filling the arterial lumen with the first set volume of the locking solution includes flowing the locking solution out of a plurality of side holes including the first side hole.

3. The method according to claim 1, wherein the first side hole is located in a distal portion of the elongated hollow body, and wherein filling the arterial lumen with the first set volume of locking solution includes flowing the locking solution out of a plurality of side holes including the first side hole.

4. The method according to claim 1, wherein the sustained-release formulation covers a terminal portion of a distal portion of the first refreshing stylet such that the first refreshing stylet refreshes a commensurate portion of the surface of the arterial lumen of the hemodialysis catheter when inserted therein.

5. The method according to claim 1, wherein the one or more anti-thrombotic agents are selected from the group consisting of nitric oxide, tissue plasminogen activator ("TPA"), and heparin.

6. The method according to claim 5, wherein the sustained-release formulation includes the nitric oxide dissolved within the sustained-release formulation, the sustained-release formulation configured to controllably off gas the nitric oxide into the surface of the arterial lumen of the hemodialysis catheter to prevent thrombus formation thereon.

7. The method according to claim 1, further comprising replacing the first refreshing stylet in the arterial lumen of the hemodialysis catheter within a predetermined amount of time or after hemodialysis.

8. The method according to claim 1, further comprising:

obtaining a second refreshing stylet;

inserting the second refreshing stylet into a venous lumen of the hemodialysis catheter such that the second refreshing stylet contacts a surface of the venous lumen of the hemodialysis catheter with the sustained-release formulation also coated on an exterior surface of the second refreshing stylet;

attaching a second needless connector coupled to a proximal portion of the second refreshing stylet to a venous Luer connector of the hemodialysis catheter to ensure an airtight seal of the venous lumen;

filling the venous lumen with a second set volume of the locking solution by flowing the locking solution from a same or different syringe into the second needless connector, through an elongated hollow body of the second refreshing stylet, and out a second side hole into the venous lumen; and replacing the second refreshing stylet in the venous lumen within a predetermined amount of time or after hemodialysis.

\* \* \* \* \*